US00PP22013P3

(12) United States Plant Patent
Zaias-Fast

(10) Patent No.: US PP22,013 P3
(45) Date of Patent: Jul. 5, 2011

(54) *POLYSCIAS* PLANT NAMED 'ARA8001'

(50) Latin Name: *Polyscias balfouriana*
Varietal Denomination: ARA8001

(76) Inventor: Magaly Zaias-Fast, Coral Springs, FL (US)

( * ) Notice: Subject to any disclaimer, the term of this patent is extended or adjusted under 35 U.S.C. 154(b) by 0 days.

(21) Appl. No.: 12/589,199

(22) Filed: Oct. 19, 2009

(65) Prior Publication Data

US 2011/0093992 P1 Apr. 21, 2011

(51) Int. Cl.
*A01H 5/00* (2006.01)

(52) U.S. Cl. ..... Plt./373; Plt./226

(58) Field of Classification Search ..... Plt./226, Plt./377, 373

See application file for complete search history.

*Primary Examiner* — June Hwu
*Assistant Examiner* — Louanne C Krawczewicz Myers

(57) ABSTRACT

A new and distinct *Polyscias balfouriana* cultivar named 'ARA8001' is disclosed, characterized by a distinct foliage variegation pattern, including a creamy yellow leaf margin and deeply lobed leaves. Plant form of the new cultivar is highly compact, with characteristically very slow growth. The new variety is a *Polyscias*, and is normally used as an ornamental plant.

1 Drawing Sheet

Figure 1:
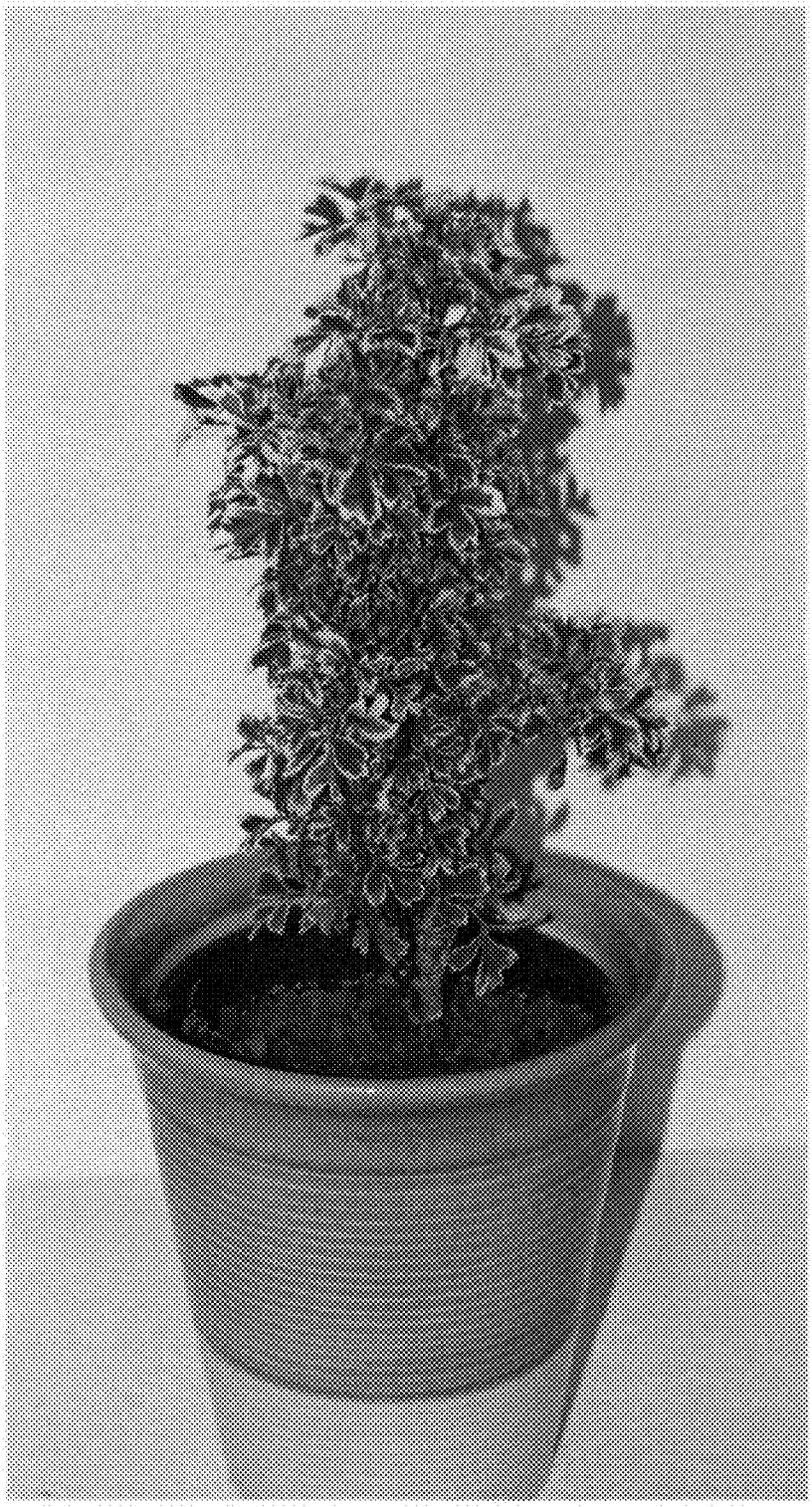

Latin name of the genus and species: *Polyscias balfouriana.*

Variety denomination: 'ARA8001'.

BACKGROUND OF THE INVENTION

The new cultivar was discovered as a chance, whole plant mutation in a commercial nursery in Bangkok, Thailand. The inventor, Magaly Zaias, a citizen of the United States, discovered the new variety as a whole plant mutation among several plants of the unpatented commercial variety, *Polyscias balfouriana.* The new variety was discovered in April 2007 by the inventor.

Asexual reproduction of the new cultivar 'ARA8001' by vegetative cuttings was performed at a commercial nursery in Bangkok Thailand in early 2008. Since that time, many generations have been reproduced, and have shown that the unique features of this cultivar are stable and reproduced true to type through successive generations.

SUMMARY OF THE INVENTION

The cultivar 'ARA8001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ARA8001.' These characteristics in combination distinguish 'ARA8001' as a new and distinct *Polyscias balfouriana* cultivar:

1. Distinctive foliage variegation pattern unlike other known *Polyscias balfouriana* cultivars.
2. Unique deeply lobed foliage.
3. Extremely compact plant growth.

PARENT COMPARISON

Plants of the new cultivar 'ARA8001' are similar to plants of the parent variety *Polyscias balfouriana* in most horticultural characteristics. However, plants of the new cultivar 'ARA8001' produce foliage of a brighter green, with a consistently thicker cream colored margin, and deep lobes. Additionally, the new variety grows much more slowly and produces much more compact plants.

COMMERCIAL COMPARISON

In addition to the parent variety, 'ARA8001' can also be compared to the unpatented, commercially known variety *Polyscias fruticosa.* The new variety produces foliage with deeper lobes and more marginal variegation. Additionally 'ARA8001' grows more slowly, and produces compact, less open plants.

BRIEF DESCRIPTION OF THE PHOTOGRAPH

The accompanying photograph in FIG. 1 illustrates in full color a typical plant of 'ARA8001' grown in a greenhouse. The pot size is a commercial 4 cm container. The plant shown is approximately 8 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'ARA8001' plants grown in a climate controlled greenhouse in Apopka, Fla., USA. Temperatures ranged from 18° C. to 22° C. at night to 18° C. to 22° C. during the day. The plant was pinched at approximately 2 months after rooting, to encourage branching. No artificial light, photoperiodic treatments or chemical treatments were given to the plants. Measurements and numerical values represent averages of typical plant types.

Botanical classification: *Polyscias balfouriana* 'ARA8001.'

PROPAGATION

Time to rooting: About 20 days at approximately 25° C.
Root description: Fine, semi-woody, free-branching roots.

PLANT

Growth habit: Upright, tender perennial.
Height: Approximately 24 cm from soil level of pot.
Plant spread: Approximately 12 cm.
Growth rate: Slow.
Branching characteristics: One main stem, after pinch 6 to 8 major lateral branches.
Diameter of main stem: Approximately 0.6 cm.
Internode length: Average 0.5 cm.
Texture of main stem: Rough, no pubescence.
Color of main stems: Near RHS Greyed-Yellow 160D.
Stem strength: Strong and somewhat flexible.
Diameter of lateral branches: Approximately 0.3 cm.
Length of lateral branches: Approximately 7 cm.
Texture of lateral branches: Smooth, no pubescence.
Color of lateral branches: Near RHS Green 141B.
Number of leaves per lateral branch: Average 6.
Age of plant described: Approximately 8 months.
Pot size of plant described: 4 inches.

FOLIAGE

Leaf:
*Arrangement.*—Alternate, odd-pinnately compound. 5 leaflets per leaf.
*Average length.*—Approximately 4.5 cm.
*Average width.*—Approximately 3.3 cm. Leaflet Average Length: 1.6 cm. Leaflet Average Width: 1.5 cm.
*Shape of blade.*—Overall shape broad oval with irregularly shaped, deeply incised leaflets.
*Aspect.*—Slightly cupped up, with moderate overall undulation.
*Apex.*—Acute.
*Base.*—Sagittate.
*Attachment.*—Stalked.
*Margin.*—Irregularly dentate.
*Texture of top surface.*—Smooth, glossy, leathery.
*Texture of bottom surface.*—Smooth, glossy, leathery.
*Color.*—Young foliage upper side: Near RHS Green 143B with margin near Yellow-Green N144D. Young foliage under side: Near RHS Green 143A. Mature foliage upper side: Near RHS Green 137A with margin near Yellow-Green 150D. Lighter colored margin width approximately 0.2 to 0.5 cm. Mature foliage under side: Near RHS Green 137D with margin near Yellow 4D. Lighter colored margin width approximately 0.1 to 0.5 cm.
*Venation.*—Type: Pinnate. Color: Upperside: Near RHS Green 137D. Underside: Near RHS Green 137A.

Petiole:
*Length.*—Average 1.8 cm.
*Width.*—Average 0.1 cm.
*Coloration.*—Near RHS Green 137A.
*Texture.*—Smooth, glossy.
*Strength.*—Soft, flexible.

Leaflet petiole:
*Length.*—Average 0.5 cm.
*Width.*—Average 0.1 cm.
*Coloration.*—Near RHS Green 143A.
*Texture.*—Smooth, glossy.
*Strength.*—Soft, flexible.

FLOWER

Flowering not observed to date.

OTHER CHARACTERISTICS

Disease resistance: Neither resistance nor susceptibility to diseases or pests normal to *Polyscias* has been observed in this variety.
Drought tolerance and temperature tolerance: Very tender perennial, low temperature damage occurs near 5° C. Tolerates high temperature to at least 40° C. Good tolerance of humid conditions. No drought tolerance, plants will begin to defoliate if soil allowed to become completely dry for 2 or more days.
Fruit/seed production: Fruits and seeds have not been observed.

What is claimed is:

1. A new and distinct cultivar of *Polyscias* plant named 'ARA8001' as herein illustrated and described.

* * * * *